(12) United States Patent
Choa et al.

(10) Patent No.: US 11,474,057 B2
(45) Date of Patent: Oct. 18, 2022

(54) THERMOCHEMICAL SENSOR AND METHOD FOR MANUFACTURING SAME

(71) Applicant: INDUSTRY-UNIVERSITY COOPERATION FOUNDATION HANYANG UNIVERSITY ERICA CAMPUS, Ansan-si (KR)

(72) Inventors: Yong-Ho Choa, Ansan-si (KR); Seil Kim, Ansan-si (KR); Yoseb Song, Ansan-si (KR)

(73) Assignee: INDUSTRY-UNIVERSITY COOPERATION FOUNDATION HANYANG UNIVERSITY ERICA CAMPUS, Ansan-si (KR)

( * ) Notice: Subject to any disclaimer, the term of this patent is extended or adjusted under 35 U.S.C. 154(b) by 667 days.

(21) Appl. No.: 16/336,386

(22) PCT Filed: Dec. 19, 2016

(86) PCT No.: PCT/KR2016/014889
§ 371 (c)(1),
(2) Date: Mar. 25, 2019

(87) PCT Pub. No.: WO2018/056522
PCT Pub. Date: Mar. 29, 2018

(65) Prior Publication Data
US 2019/0234894 A1   Aug. 1, 2019

(30) Foreign Application Priority Data
Sep. 26, 2016  (KR) .......................... 10-2016-0122903

(51) Int. Cl.
*G01N 25/32*   (2006.01)
*G01N 33/00*   (2006.01)
*G01N 27/407*  (2006.01)

(52) U.S. Cl.
CPC .......... *G01N 25/32* (2013.01); *G01N 27/4071* (2013.01); *G01N 27/4075* (2013.01); *G01N 33/005* (2013.01)

(58) Field of Classification Search
CPC ............................. G01N 25/32; G01N 33/005
See application file for complete search history.

(56) References Cited

U.S. PATENT DOCUMENTS

| 2010/0147684 A1* | 6/2010 | Park ................... G01N 27/127 204/431 |
| 2016/0013389 A1* | 1/2016 | Choa ................... G01N 27/127 438/54 |

FOREIGN PATENT DOCUMENTS

| JP | 2006-090822 A | 4/2006 |
| JP | 2012-004528 A | 1/2012 |

(Continued)

OTHER PUBLICATIONS

Kim, S. et al. "Thermochemical hydrogen sensor based on Pt-coated nanofiber catalyst deposited on pyramidally textured thermoelectric film," Applied Surface Science 415 (2017) 119-125. Available online Oct. 5, 2016 (Year: 2016).*

(Continued)

*Primary Examiner* — Jennifer Wecker
*Assistant Examiner* — Michelle Adams
(74) *Attorney, Agent, or Firm* — Sughrue Mion, PLLC

(57) ABSTRACT

A thermochemical sensor is provided. The thermochemical sensor comprises: a substrate structure comprising a thermoelectric surface having concave portions and convex portions; a base fiber disposed on the thermoelectric surface of the substrate structure; and a catalyst layer that conformally covers the thermoelectric surface of the substrate structure and the base fiber.

16 Claims, 13 Drawing Sheets

(56) References Cited

FOREIGN PATENT DOCUMENTS

| KR | 10-2008-0069095 A | 7/2008 |
|---|---|---|
| KR | 10-2010-0008550 A | 1/2010 |
| KR | 10-2010-0067972 A | 6/2010 |
| KR | 10-2014-0106812 A | 9/2014 |
| KR | 10-2015-0066322 A | 6/2015 |

OTHER PUBLICATIONS

Kim, S. et al. "Thermochemical hydrogen sensor based on chalcogenide nanowire arrays," Nanotechnology 26 (2015) 145503 (11pp), Published Mar. 19, 2015 (Year: 2015).*

Zhang, J. et al. "Preparation and characteristics of Pt/ACC catalyst for thermoelectric thin film hydrogen sensor," Sensors and Actuators B 128 (2007) 266-272 (Year: 2007).*

Seil Kim "Thermochemical Hydrogen Sensor Based on Pt Nanofiber Catalyst Coated Textured Shape Thermoelectric Thin Film", The 14th International Symposium on Novel and Nano Materials, Jul. 5, 2016, Budapest Hungary, 5 pages.

International Search Report for PCT/KR2016/014889, dated May 26, 2017.

* cited by examiner

[FIG. 1]
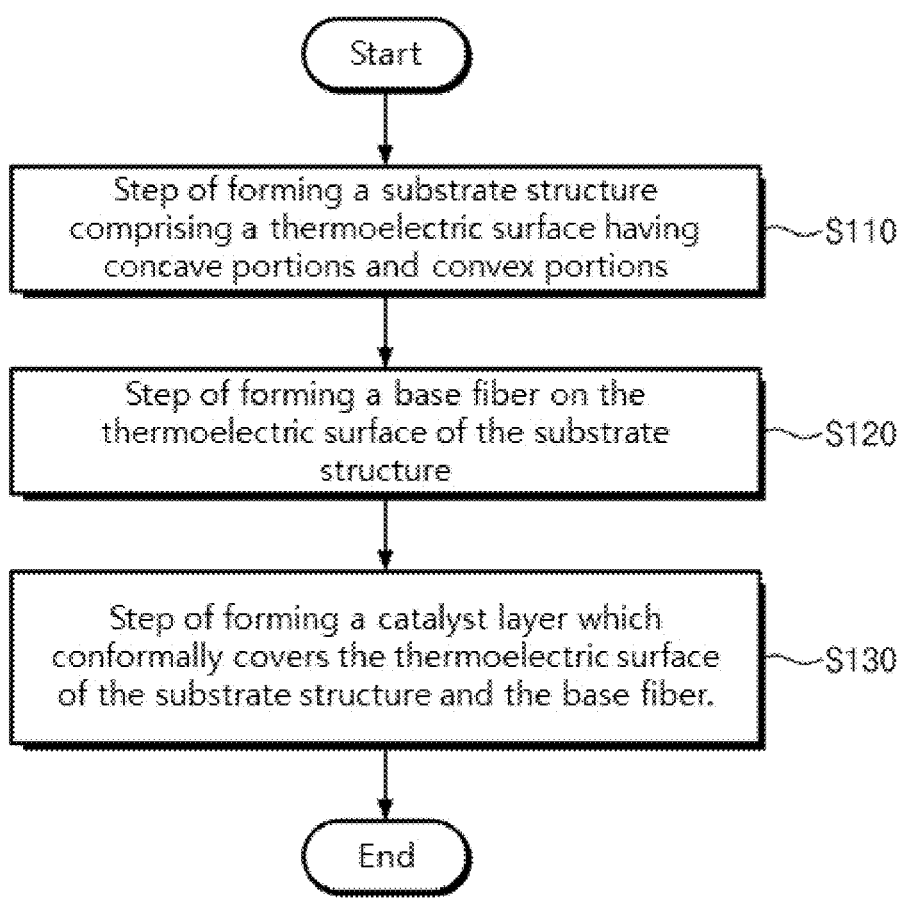

[FIG. 2]
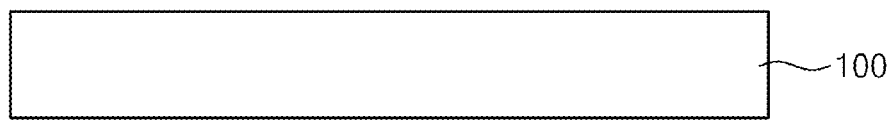
[FIG. 3]
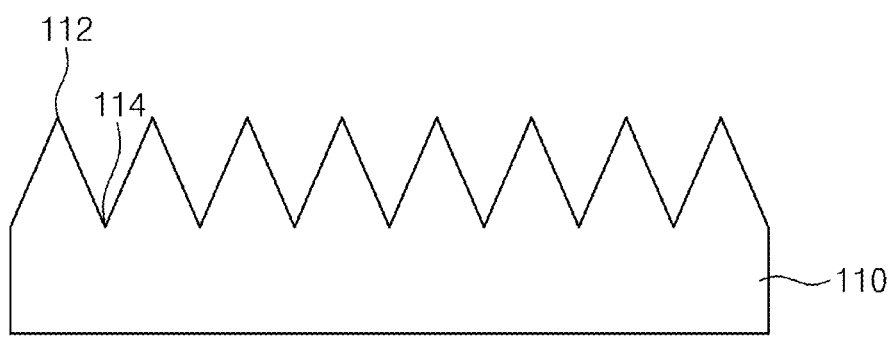

[FIG. 4]
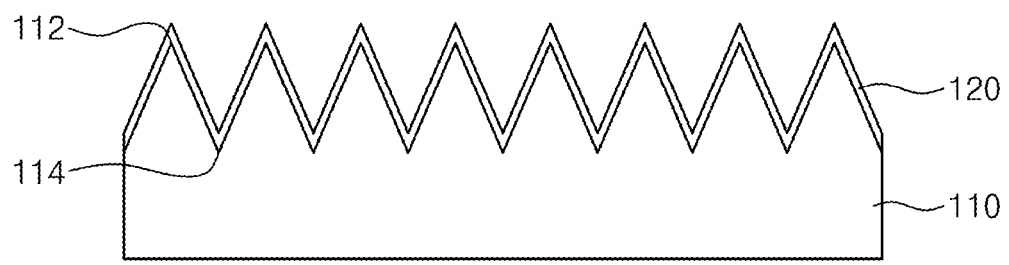
[FIG. 5]
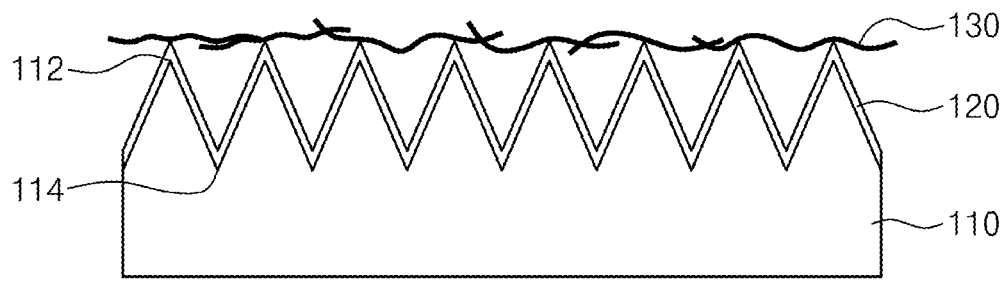

【FIG. 6】
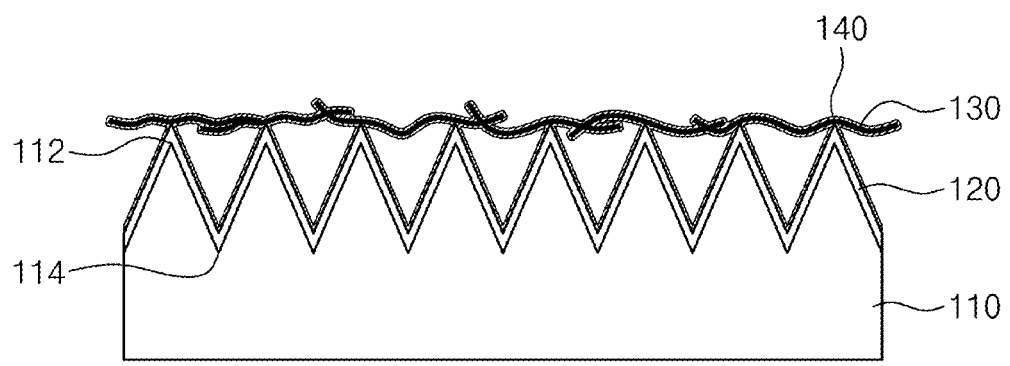

[FIG. 7A] [FIG. 7B]
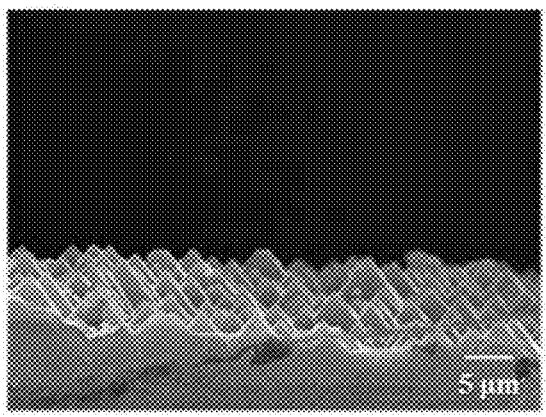 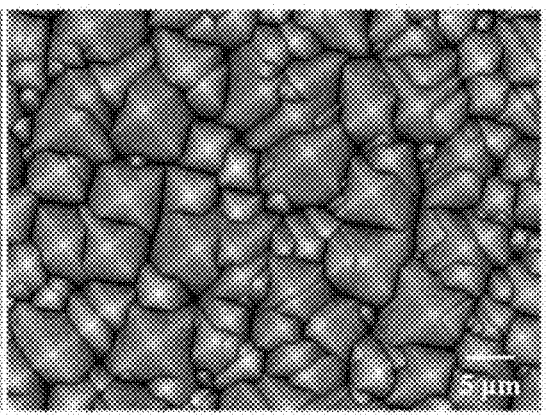
[FIG. 8A] [FIG. 8B]
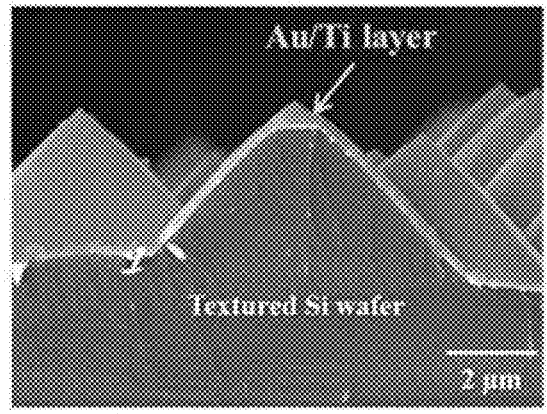 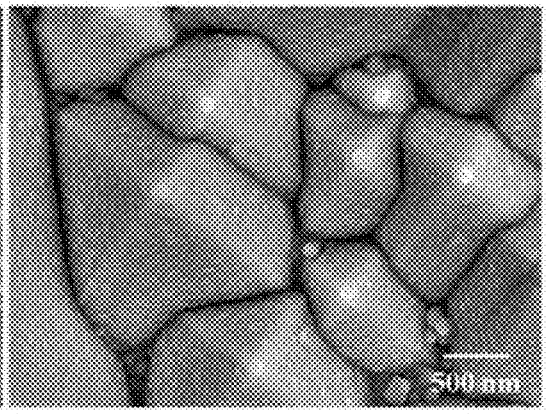

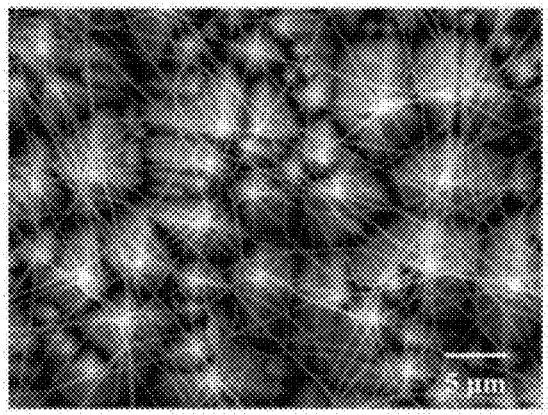
[FIG. 9A]
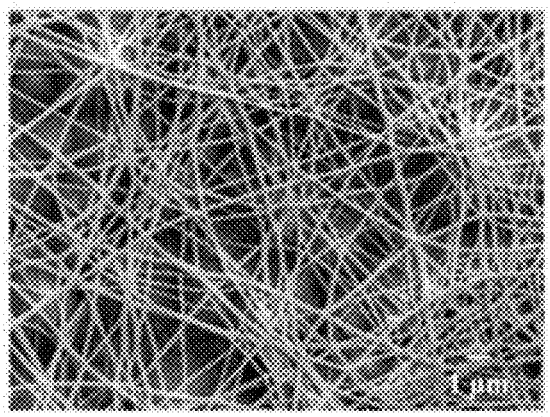
[FIG. 9B]
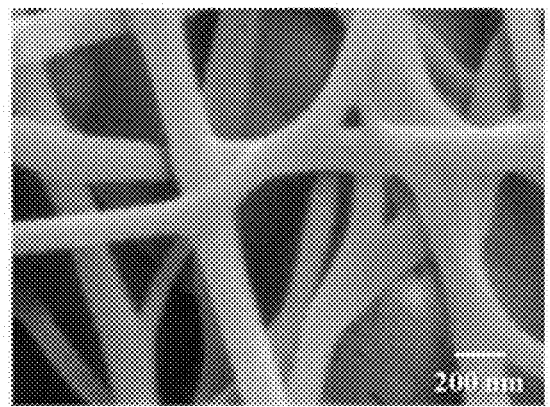
[FIG. 9C]

[FIG. 10A] [FIG. 10B]
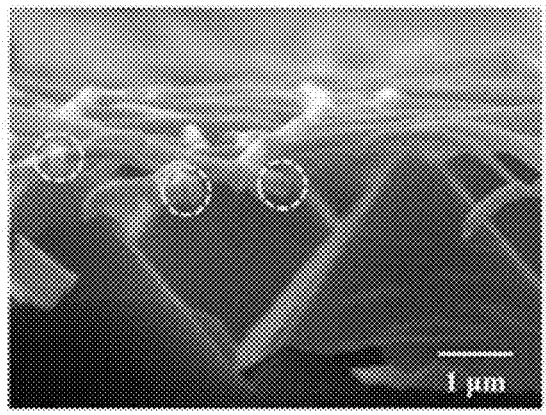 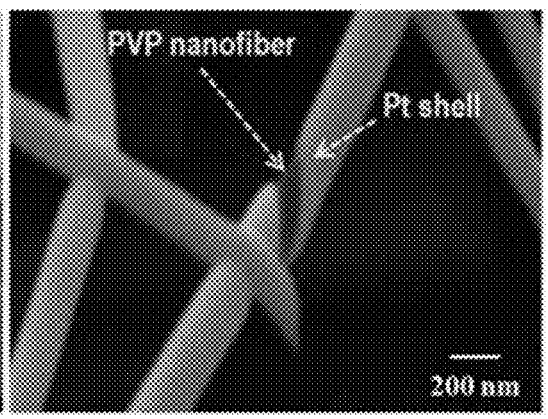

[FIG. 12]
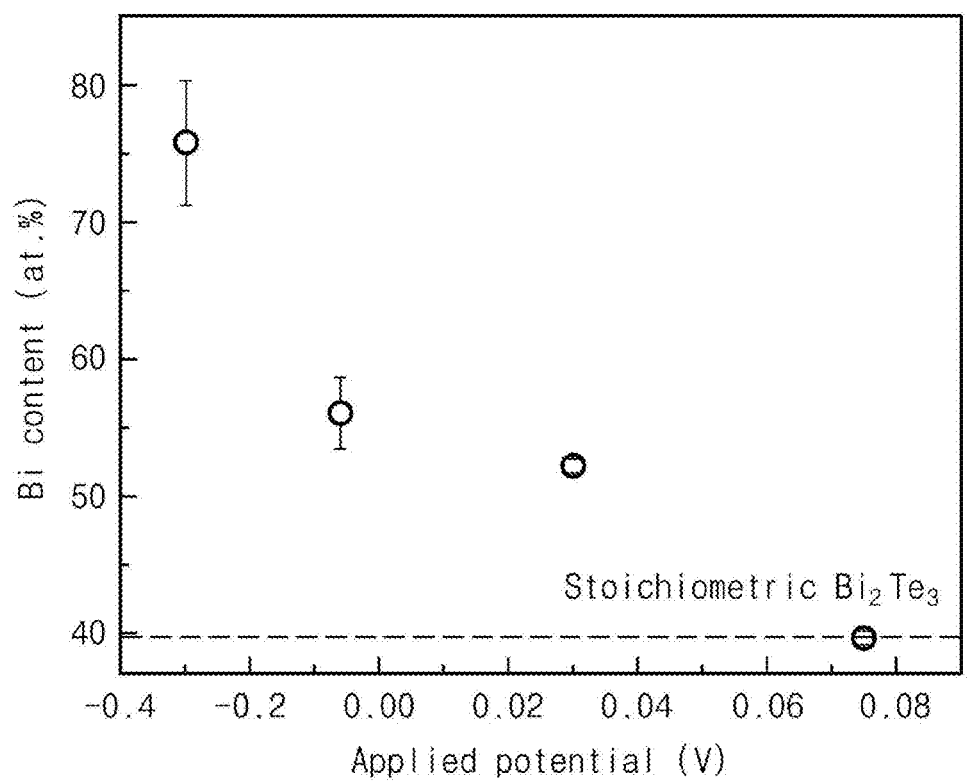

[FIG. 13]
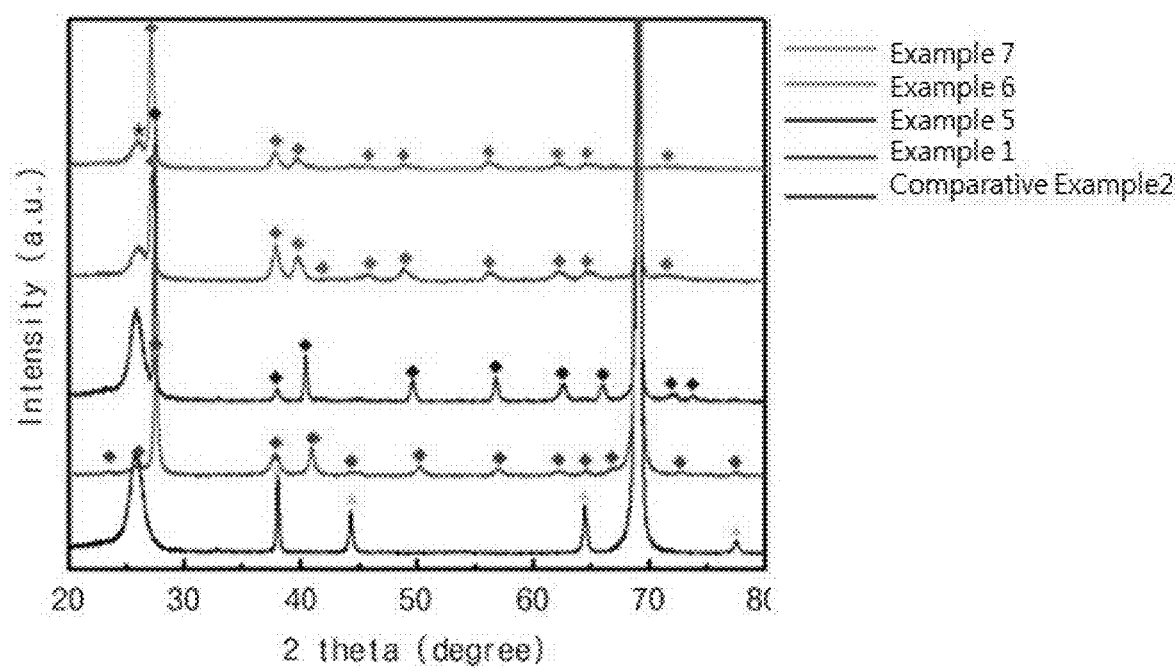

[FIG. 14A]
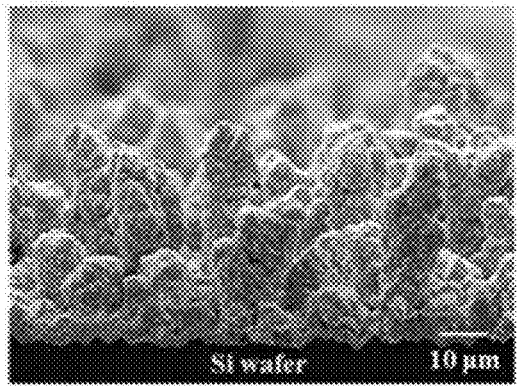
[FIG. 14B]
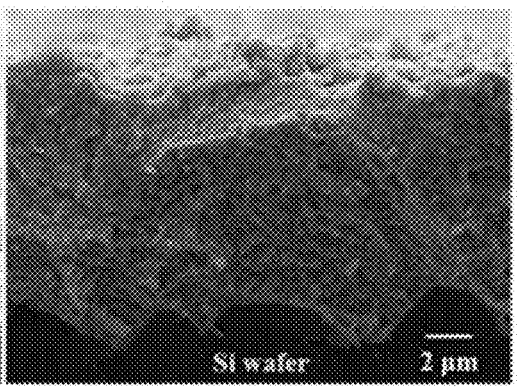
[FIG. 14C]
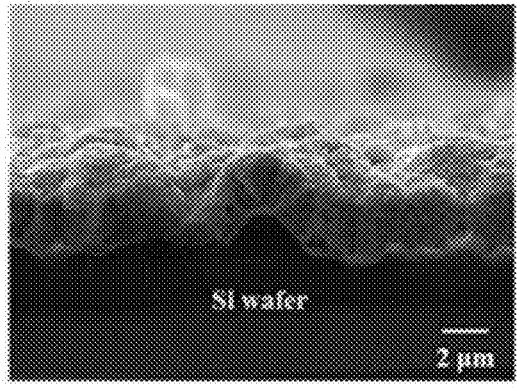
[FIG. 14D]
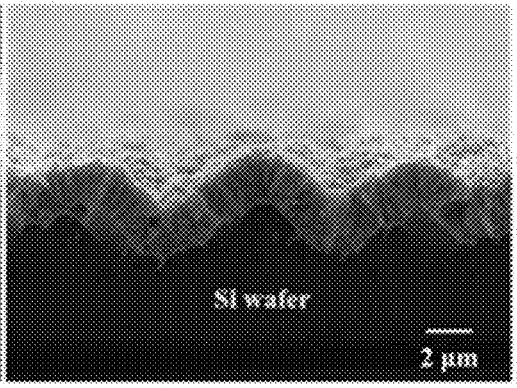

[FIG. 15]
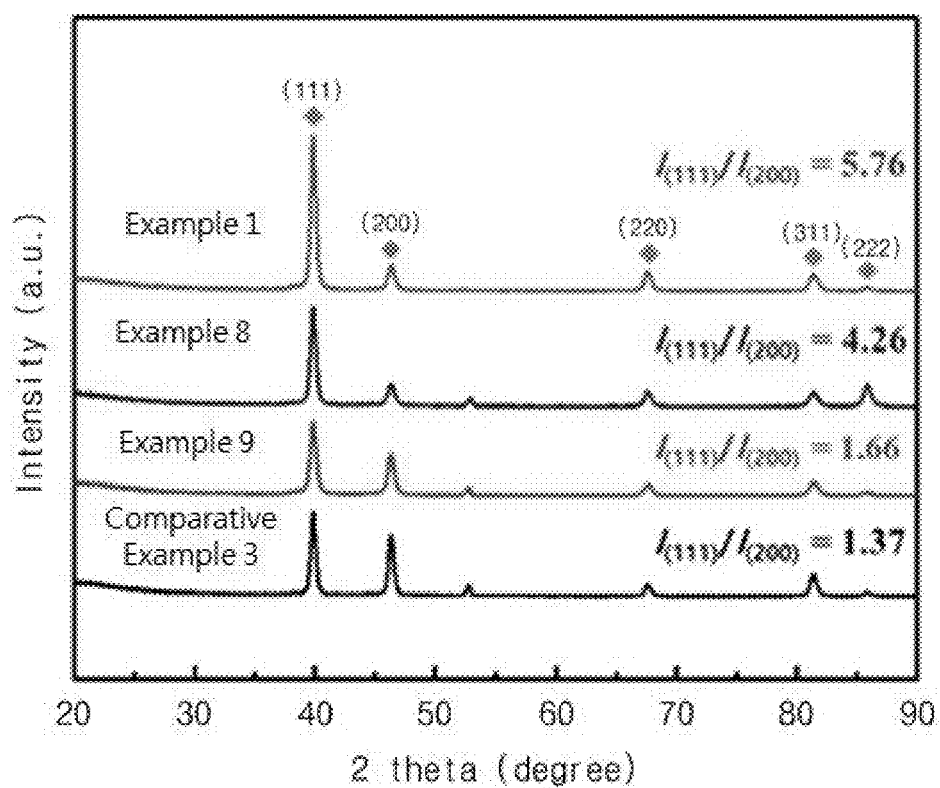

[FIG. 16A]
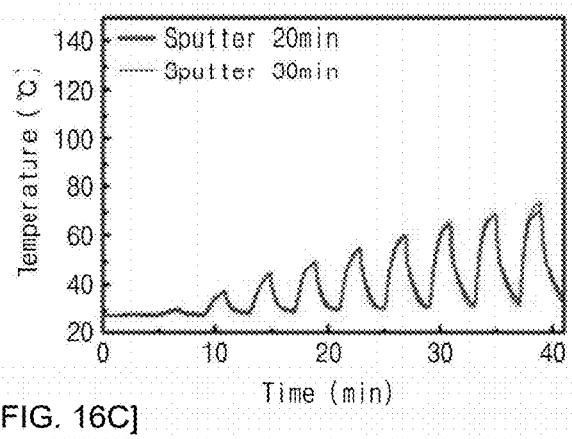
[FIG. 16B]
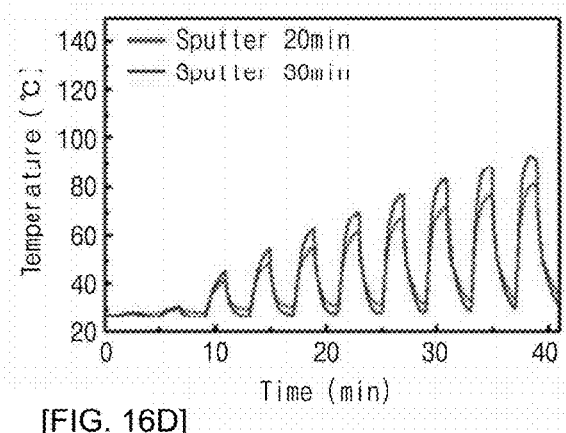
[FIG. 16C]
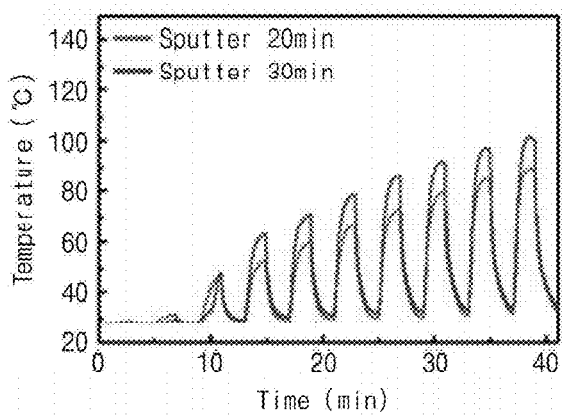
[FIG. 16D]
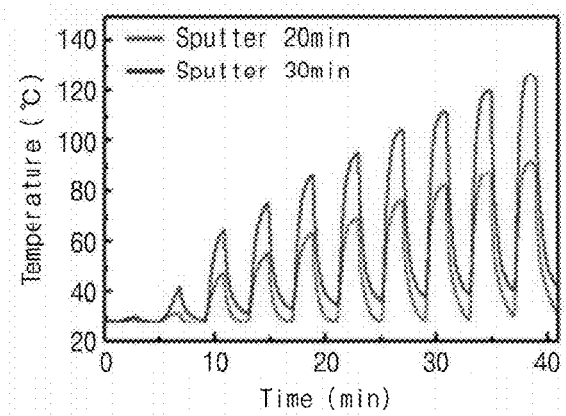

[FIG. 17A]
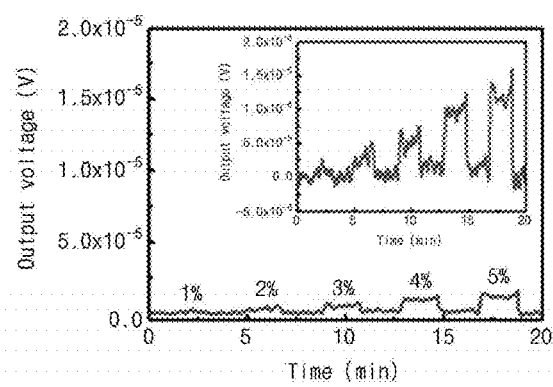
[FIG. 17B]
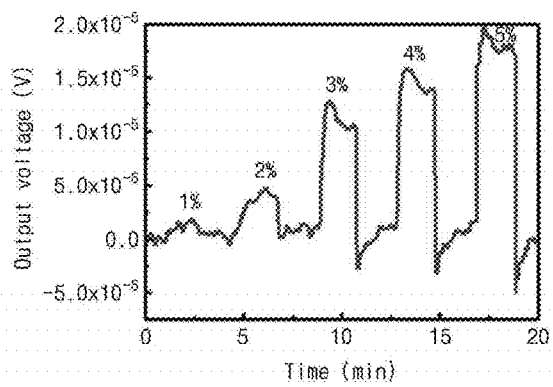

THERMOCHEMICAL SENSOR AND METHOD FOR MANUFACTURING SAME

This Application is a National Stage of International Application No. PCT/KR2016/014889 filed Dec. 19, 2016, claiming priority based on Korean Patent Application No. 10-2016-0122903 filed Sep. 26, 2016.

TECHNICAL FIELD

The present invention relates to a thermochemical sensor and a method for fabricating the same, and more particularly to a thermochemical sensor including a substrate structure, a base fiber and a catalyst layer and having an increased area for reaction with a target gas, and a method for fabricating the same.

BACKGROUND ART

Recently, hydrogen gas has attracted attention for use in various fields, including automobile fuel cells, hydrogen engines, semiconductor thin-film processing, and so on. Particularly, hydrogen as an energy source has attracted attention as a future clean fuel because it can suppress the emission of carbon dioxide. However, hydrogen gas has a wide explosive concentration range of 4 to 75%, and thus needs to be sensed in a more precise and complete manner than other combustible gases in sensor characteristics. Therefore, a hydrogen sensor, which can be actually commercialized and used, should be able to sense hydrogen at low concentration and in a wide range of gas concentration, should not be influenced by either gases other than hydrogen gas, or water vapor (including humidity), temperature, etc., and should satisfy conditions such as high sensing accuracy, miniaturization and the like.

Accordingly, various devices for hydrogen sensing have been developed. For example, Korean Patent Application Laid-Open Publication No. 10-2009-0082900 (Application No.: 10-2009-7010282; Applicant Atsumitec Co., Ltd.) provides a hydrogen sensing device capable of hydrogen gas, which includes: a thin film layer formed on the top surface of the planar light transmission medium of a hydrogen sensor; a catalyst layer formed on the surface of the thin film layer; a first interface formed between the planar light transmission medium and the thin film layer; and a substrate joined to the bottom surface of the planar optical transmission medium to form a second interface between the substrate and the planar optical transmission medium, the hydrogen sensing device being configured such that light emitted from a light source is spread and introduced into the first end portion of the planar optical transmission medium, and then reflected repeatedly between the first interface and the second interface and transmitted to the second end portion of the planar optical transmission medium, and the light is emitted from the second end portion is transmitted to an optical sensor by an exit light-collecting section, and when the thin film layer is hydrogenated by the catalyst layer that came into contact with hydrogen, the amount of light reflected from the first interface is reduced, and the amount of light reduced is detected by the optical sensor, thereby detecting hydrogen gas.

In addition, fabrication technologies for various devices capable of sensing hydrogen have been researched and developed.

DISCLOSURE

Technical Problem

One technical problem to be solved by the present invention is to provide a low-cost thermochemical sensor and a fabrication method therefor.

Another technical problem to be solved by the present invention is to provide a thermochemical sensor having an increase area for reaction with a target gas and a fabrication method therefor.

Still another technical problem to be solved by the present invention is to provide a thermochemical sensor including a catalyst having improved characteristics and a fabrication method therefor.

Yet another technical problem to be solved by the present invention is to provide a highly efficient and highly reliable thermochemical sensor and a fabrication method therefor.

Technical problems to be solved by the present invention are not limited to the above-described technical problems.

Technical Solution

To solve the above-described technical problems, the present invention provides a thermochemical sensor.

According to one embodiment, the thermochemical sensor may include: a substrate structure including a thermoelectric surface having concave portions and convex portions; a base fiber disposed on the thermoelectric surface of the substrate structure; and a catalyst layer which conformally covers the thermoelectric surface of the substrate structure and the base fiber.

According to one embodiment, the base fiber may be hung over the concave portions and the convex portions, so that at least a portion of the base fiber may be spaced apart from the substrate structure by the concave portions and the convex portions.

According to one embodiment, the catalyst layer may be configured to cover the at least a portion of the base fiber spaced apart from the substrate structure.

According to one embodiment, the catalyst layer may be configured to surround the base fiber.

According to one embodiment, the catalyst layer may be configured to react with a target gas, and the proportion of the crystal surface of the catalyst that reacts with the target gas may increase as the amount of the base fiber increases.

According to one embodiment, the crystal surface of the catalyst layer may include the (111) plane of the catalyst layer.

According to one embodiment, when the catalyst reacts with the target gas, heat may be generated in the catalyst layer, and due to the generated heat, an electrical signal may be generated in the thermoelectric layer.

According to one embodiment, the substrate structure may include: a substrate having the concave portions and the convex portions; and a thermoelectric layer which conformally covers the substrate and which provides the thermoelectric surface.

According to one embodiment, the thickness of the thermoelectric layer may be thinner than the level difference between the concave portion and the convex portion.

According to one embodiment, the thermoelectric layer may include a chalcogenide-based material.

According to one embodiment, the thermoelectric layer may include $Bi_2Te_3$.

According to one embodiment, the base fiber may include a polymer material, and the polymer may include any one of PVP (polyvinylpyrrolidone), polyethylene oxide, polyvinyl acetate, polyvinyl alcohol, polylactic acid, polyamide, polyester, and polypropylene.

To solve the above-described technical problems, the present invention provides a method for fabricating a thermochemical sensor.

According to one embodiment, the method for fabricating the thermochemical sensor may include the steps of: forming a substrate structure including a thermoelectric surface having concave portions and convex portions; forming a base fiber disposed on the thermoelectric surface of the substrate structure; and forming a catalyst layer that conformally covers the thermoelectric surface of the substrate structure and the base fiber.

According to one embodiment, the step of preparing the substrate structure may include the steps of: preparing a substrate having the concave portions and the convex portions; and forming on the substrate a thermoelectric layer that provides the thermoelectric surface.

According to one embodiment, the step of preparing the substrate having the concave portions and the convex portions may include the steps of: preparing a preliminary substrate; immersing the preliminary substrate in an aqueous etching solution; and heat-treating the immersed preliminary substrate.

According to one embodiment, the step of forming the base fiber may include a step of spinning a polymer solution onto the thermoelectric surface of the substrate structure.

Advantageous Effects

According to an embodiment of the present invention, there may be a thermochemical sensor including: a substrate structure including a thermoelectric surface having concave portions and convex portions; a base fiber disposed on the thermoelectric surface of the substrate structure; and a catalyst layer that conformally covers the thermoelectric surface of the substrate structure and the base fiber. The substrate structure may include: a substrate having the concave portions and the convex portions; and a thermoelectric layer which conformally covers the substrate and which provides the thermoelectric surface. Furthermore, the thermoelectric layer may be formed by electrochemical deposition. Accordingly, the thermochemical sensor may be provided at low costs through a simple process.

The base fiber may be hung over the concave portions and the convex portions, so that at least a portion of the base fiber may be spaced apart from the substrate structure by the concave portions and the convex portions. The catalyst layer may completely cover the base fiber. Accordingly, a thermochemical sensor having an increased area for reaction with a target gas may be provided.

In addition, the catalyst layer may be configured to react with the target gas, and the proportion of the crystal surface of the catalyst layer that reacts with the target gas may increase as the amount of the base fiber increases. Accordingly, a thermochemical sensor including a catalyst having improved characteristics may be provided. As a result, a highly efficient and highly reliable thermochemical sensor may be provided.

DESCRIPTION OF DRAWINGS

FIG. 1 is a flow chart illustrating a method for fabricating a thermochemical sensor according to an embodiment of the present invention.

FIGS. 2 to 6 are views illustrating a process for fabricating a thermochemical sensor according to an embodiment of the present invention.

FIGS. 7A-7B show optical images of a substrate according to an Example of the present invention.

FIGS. 8A-8B show optical images of a substrate and seed layer according to an Example of the present invention.

FIGS. 9A-9C show optical images of a base fiber and catalyst layer according to an Example of the present invention.

FIGS. 10A-10B show optical images of a thermochemical sensor according to an Example of the present invention.

FIGS. 11 to 13 depict graphs showing characteristics depending on changes of thermoelectric layers in thermochemical sensors according to the Examples of the present invention and Comparative Examples.

FIGS. 14A-14D shows SEM images of thermoelectric layers according to the Examples of the present invention.

FIG. 15 is a graph showing characteristics depending on the time of spinning of a base fiber in thermochemical sensors according to the Examples of the present invention and a Comparative Example.

FIGS. 16A-16D and FIGS. 17A-17B depict graphs showing hydrogen concentration-dependent changes in the characteristics of thermochemical sensors according to the Examples of the present invention and Comparative Examples.

MODE FOR INVENTION

Hereinafter, exemplary embodiments of the present invention will be described in detail with reference to the accompanying drawings. However, the technical spirit of the present invention is not limited to the embodiments described herein and may also be embodied in different forms. Rather, the embodiments disclosed herein are provided so that this disclosure will be thorough and complete, and will fully convey the scope of the present invention to those skilled in the art.

When a first element is referred to as being "on" another element layer, it not only refers to a case where the first element is formed directly on the other element but also a case where a third element exists therebetween. In drawings, the thicknesses of layers and regions are exaggerated for effective description of the technical contents.

Furthermore, terms such as first, second, third and the like are used in various embodiments of the specification in order to describe various elements, but these elements should not be limited by these terms. These terms are only used to distinguish one element from another element. Thus, an element referred to as a first element in any one embodiment may also be referred to as a second element. Each embodiment described and illustrated herein includes its complementary embodiment as well. Moreover, as used herein, the term "and/or," includes any and all combinations of one or more of the associated listed items.

Singular expressions herein include plural expressions unless specified otherwise in the context thereof. In this specification, the terms "comprise", "have", etc., are intended to denote the existence of mentioned characteristics, numbers, steps, elements, or combinations thereof, but do not exclude the possibility of existence or addition of one or more other characteristics, numbers, steps, elements, or combinations thereof. As used herein, "connecting" is intended to include both indirectly connecting and directly connecting a plurality of elements.

In the following description, when the detailed description of a relevant known element is determined to unnecessarily obscure the subject matter of the present invention, it will be omitted.

FIG. 1 is a flow chart illustrating a method for fabricating a thermochemical sensor according to an embodiment of the present invention, and FIGS. 2 to 6 are process sectional views illustrating a process for fabricating a thermochemical sensor according to an embodiment of the present invention.

Referring to FIGS. 1 and 2, a preliminary substrate 100 is prepared. According to an embodiment, the preliminary substrate 100 may be a p-type silicon substrate. Alternatively, the preliminary substrate 100 may be a semiconductor substrate, a compound semiconductor substrate, a glass substrate, a plastic substrate, or a metal substrate.

An oxide layer may be produced on the surface of the preliminary substrate 100. The oxide layer may be a native oxide layer. The oxide layer may be removed with an acidic solution. According to one embodiment, the acid solution may be an HF solution. Alternatively, the acidic solution may be HBr, HI, or HCl.

Referring to FIGS. 1 and 3, concave portions 114 and convex portions 112 may be formed on one surface of the base substrate 100, thereby providing a substrate 100. Specifically, the step of forming the substrate 100 having the concave portions 114 and the convex portions 112 may include a step of immersing the preliminary substrate 100 in an aqueous etching solution, and a step of heat-treating the immersed preliminary substrate 100. For example, the aqueous etching solution may contain TMAH (tetramethyl ammonium hydroxide) and IPA (isopropyl alcohol). For example, the step of heat-treating may be performed at a temperature of 85° C. for 30 minutes.

Referring to FIGS. 1 and 4, a thermoelectric layer 120 may be formed on the substrate 100 having the concave portions 114 and the convex portions 112. As a result, a substrate structure including a thermoelectric surface having the concave portions 114 and the convex portions 112 may be formed (S110). Specifically, the substrate structure may include: the substrate 110 having the concave portions 114 and the convex portions 112; and the thermoelectric layer 120 which conformally covers the substrate 110 and which provides the thermoelectric surface.

The thickness of the thermoelectric layer 120 may be thinner than the level difference between the concave portion 114 and the convex portion 112. The thermoelectric layer 120 may conformally cover the concave portions 114 and the convex portions 112. Accordingly, the thermoelectric layer may include the concave portions 114 and the convex portions 112. According to one embodiment, the thermoelectric layer 120 may be formed by electrochemical deposition. According to one embodiment, the thermoelectric layer 120 may include a chalcogenide-based material. For example, the thermoelectric layer 120 may be $Bi_2Te_3$.

According to one embodiment, the thermoelectric layer 120 may be formed using an electrolyte and a three-electrode system. The electrolyte may include a bismuth (Bi) precursor, a tellurium (Te) precursor, and an acid. For example, the bismuth precursor may be $Bi(NO_3)_3 5H_2O$. For example, the tellurium precursor may be $TeO_2$. For example, the acid may be $HNO_3$. The three-electrode system may include a counter electrode, a reference electrode, and a working electrode. For example, the counter electrode may be a platinum-coated titanium strip. For example, the reference electrode may be Ag/AgCl. For example, the working electrode may be Au/Ti. The working electrode may be a seed layer that facilitates formation of the thermoelectric layer.

Referring to FIGS. 1 and 5, a base fiber 130 is formed on the thermoelectric surface of the substrate structure (S120). According to one embodiment, the base fiber 130 may be formed by electrospinning. The step of forming the base fiber 130 may include a step of spinning a polymer solution onto the thermoelectric surface of the substrate structure. The amount of the base fiber 130 may be adjusted depending on the time of spinning of the polymer solution. According to one embodiment, the polymer solution may contain a polymer, an alcohol, and a solvent.

For example, the polymer may be any one of PVP (polyvinylpyrrolidone), polyethylene oxide, polyvinyl acetate, polyvinyl alcohol, polylactic acid, polyamide, polyester, and polypropylene. For example, the alcohol may be ethanol. For example, the solvent may be DI water.

The base fiber 130 may be hung over the concave portions 114 and the convex portions 112, so that at least a portion of the base fiber 130 may be spaced apart from the substrate structure by the concave portions 114 and the convex portions 112. In other words, the base fiber 130 may be supported and hung by the convex portions 112. Furthermore, the base fiber 130 may be formed to be spaced apart from the surface of the concave portions 114 between the convex portions 112. Moreover, at least a portion of the base fiber 130 may be in contact with the convex portions 112. In addition, the base fiber 130 may be a web form which randomly contacts the surface of substrate structure.

Referring to FIGS. 1 and 6, a catalyst layer 140 may be formed, which conformally covers the thermoelectric surface of the substrate structure and the base fiber 130 (S130). According to one embodiment, the catalyst may be formed by a sputtering method. According to other embodiments, the catalyst layer may be formed by chemical vapor deposition (CVD), physics vapor deposition (PVD), or atomic layer deposition (ALD). According to one embodiment, the catalyst layer 140 may be platinum (Pt). The catalyst layer 140 may be configured to cover at least a portion of the base fiber 130 spaced apart from the substrate structure. In addition, the catalyst layer 140 may be configured to surround the base fiber 130.

The catalyst layer 140 is capable of reacting with a target gas. The catalyst layer 140 may include a crystal surface that reacts with the target gas. The proportion of the crystal surface may increase as the amount of the base fiber 130 increases. For example, the target gas may be hydrogen. The crystal surface of the catalyst layer 140 may include the (111) plane of the catalyst layer. The catalyst layer 140 may react with the target gas, and thus heat is generated in the catalyst layer, and due to the generated heat, an electrical signal may be generated in the thermoelectric layer.

Unlike the above-described embodiment of the present invention, in the case of either a thermochemical sensor which does not include the base fiber 130 or a thermochemical sensor fabricated by a method in which particles are disposed on the concave portions 114 and the convex portions 112 and the catalyst layer 140 that covers the particles is formed, the surface area in which the catalyst layer 140 reacts with the target gas may decrease. This may reduce the characteristics of the catalyst.

However, the thermochemical sensor according to the embodiment of the present invention may include: the base fiber 130 which is hung over the concave portions 114 and the convex portions 112 and at least a portion of which is spaced apart from the substrate structure by the concave portions 114 and the convex portions 112; and the catalyst layer 140 which conformally covers the base fiber 130. In addition, the catalyst layer 140 may completely cover the hung base fiber 130. Accordingly, a thermochemical sensor having an increased area for reaction with the target gas may be provided.

Furthermore, the amount of the base fiber 130 may be adjusted depending on the time of spinning of the polymer solution. As the amount of the base fiber 130 increases, the proportion of the crystal surface of the catalyst layer that reacts with the target gas may increase. Accordingly, a thermochemical sensor having an increased area for reaction with the target gas may be provided. As a result, a thermochemical sensor having improved characteristics of the catalyst that reacts with the target gas may be provided.

Hereinafter, the results of evaluating the characteristics of the thermochemical sensor according to the above-described embodiment of the present invention will be described.

Fabrication of Thermochemical Sensor According to Example 1

A p-type silicon preliminary substrate was prepared. The preliminary substrate was immersed in 10 wt % HF solution at room temperature (25° C.) for 10 minutes to remove the oxide layer. An aqueous etching solution was prepared. The aqueous etching solution was prepared with 2 wt % TMAH (tetramethyl ammonium hydroxide) and 8 wt % IPA (isopropyl alcohol). The preliminary substrate from which the oxide layer was removed was immersed in the aqueous etching solution, heat-treated at a temperature for 85° C., for 30 minutes, thereby preparing a substrate including concave portions and convex portions. On the substrate including the concave portions and the convex portions, an Au/Ti seed layer having a thickness of 200 nm was formed by an E-beam process.

On the substrate having the seed layer formed thereon, a $Bi_2Te_3$ thermoelectric layer was formed. The thermoelectric layer was formed by electrochemical deposition for 30 minutes in a three-electrode system while applying a voltage of 75 mV. The electrolyte used in the electrochemical deposition was prepared using 1 M $HNO_3$, 10 mM $TeO_2$, and 70 mM $Bi(NO_3)_3 5H_2O$. In addition, the three-electrode system included a platinum-coated titanium strip as a counter electrode, an Ag/AgCl as a reference electrode, and Au/Ti as a working electrode.

A 10 wt % PVP polymer solution was prepared. The polymer solution was prepared by stirring 5 g of PVP (polyvinylpyrrolidone) having a molecular weight of 1,300,000 g/mol, 2 g of ethanol, and 3 g of DI water at room temperature for 3 hours.

On the thermoelectric surface of the substrate having the thermoelectric layer formed thereon, the polymer solution was applied by electrospinning, thereby forming a base fiber. The electrospinning was performed using a 10-ml plastic syringe, a 30-gauge tip, and a voltage of 20 kV. Furthermore, the polymer solution was supplied through the plastic syringe at a rate of 0.4 ml/hr. In addition, the electrospinning was performed in an environment with a temperature of 40° C. and a relative humidity of 20%. On the thermoelectric surface and the base fiber, platinum (Pt) was coated by a sputtering method to form a catalyst layer, thereby fabricating a thermochemical sensor.

Fabrication of Thermochemical Sensor According to Example 2

A substrate including concave layers, convex portions and a seed layer was prepared as described in Example 1 above. On the substrate, a thermoelectric layer was formed in the same manner as described in Example 1 above, except that 40 mM $Bi(NO_3)_3 5H_2O$ was used in formation of the thermoelectric layer. Thereafter, a base fiber and a catalyst were formed as described in Example 1 above, thereby fabricating a thermochemical sensor.

Fabrication of Thermochemical Sensor According to Example 3

A substrate including concave layers, convex portions and a seed layer was prepared as described in Example 1 above. On the substrate, a thermoelectric layer was formed in the same manner as described in Example 1 above, except that 10 mM $Bi(NO_3)_3 5H_2O$ was used in formation of the thermoelectric layer. Thereafter, a base fiber and a catalyst were formed as described in Example 1 above, thereby fabricating a thermochemical sensor.

Fabrication of Thermochemical Sensor According to Example 4

A substrate including concave layers, convex portions and a seed layer was prepared as described in Example 1 above. On the substrate, a thermoelectric layer was formed in the same manner as described in Example 1 above, except that 5 mM $Bi(NO_3)_3 5H_2O$ was used in formation of the thermoelectric layer. Thereafter, a base fiber and a catalyst were formed as described in Example 1 above, thereby fabricating a thermochemical sensor.

Fabrication of Thermochemical Sensor According to Example 5

A substrate including concave layers, convex portions and a seed layer was prepared as described in Example 1 above. On the substrate, a thermoelectric layer was formed in the same manner as described in Example 1 above, except that a voltage of 30 mV was applied in formation of the thermoelectric layer. Thereafter, a base fiber and a catalyst were formed as described in Example 1 above, thereby fabricating a thermochemical sensor.

Fabrication of Thermochemical Sensor According to Example 6

A substrate including concave layers, convex portions and a seed layer was prepared as described in Example 1 above. On the substrate, a thermoelectric layer was formed in the same manner as described in Example 1 above, except that a voltage of −6 mV was applied in formation of the thermoelectric layer. Thereafter, a base fiber and a catalyst were formed as described in Example 1 above, thereby fabricating a thermochemical sensor.

Fabrication of Thermochemical Sensor According to Example 7

A substrate including concave layers, convex portions and a seed layer was prepared as described in Example 1 above. On the substrate, a thermoelectric layer was formed in the same manner as described in Example 1 above, except that a voltage of −30 mV was applied in formation of the thermoelectric layer. Thereafter, a base fiber and a catalyst were formed as described in Example 1 above, thereby fabricating a thermochemical sensor.

Fabrication of Thermochemical Sensor According to Example 8

A substrate structure including concave layers, convex portions, a seed layer and a thermoelectric layer was prepared as described in Example 1 above. On the substrate structure, a base fiber was formed in the same manner as described in Example 1 above, except that the electrospinning was performed for 5 minutes. Thereafter, a catalyst layer was formed as described in Example 1, thereby fabricating a thermochemical sensor.

Fabrication of Thermochemical Sensor According to Example 9

A substrate structure including concave layers, convex portions, a seed layer and a thermoelectric layer was prepared as described in Example 1 above. On the substrate structure, a base fiber was formed in the same manner as described in Example 1 above, except that the electrospinning was performed for 1 minute. Thereafter, a catalyst layer was formed as described in Example 1, thereby fabricating a thermochemical sensor.

Fabrication of Thermochemical Sensor According to Comparative Example 1

A substrate including concave layers, convex portions and a seed layer was prepared as described in Example 1 above. On the substrate, a thermoelectric layer was formed in the same manner as described in Example 1 above, except that $Bi(NO_3)_3 5H_2O$ was not used in formation of the thermoelectric layer. Thereafter, a base fiber and a catalyst were formed as described in Example 1 above, thereby fabricating a thermochemical sensor.

Fabrication of Thermochemical Sensor According to Comparative Example 2

A substrate including concave layers, convex portions and a seed layer was prepared as described in Example 1 above. Gold (Au) was deposited on the substrate to form a thermoelectric layer. Thereafter, a base fiber and a catalyst were formed as described in Example 1 above, thereby fabricating a thermochemical sensor.

Fabrication of Thermochemical Sensor According to Comparative Example 3

A substrate structure including concave layers, convex portions, a seed layer and a thermoelectric layer was prepared as described in Example 1 above. On the substrate structure, a catalyst layer was formed as described in Example 1 above without forming a base fiber, thereby fabricating a thermochemical sensor.

Conditions for fabricating the thermochemical sensors according to Examples 1 to 9 and Comparative Example 1 are summarized in Table 1 below.

TABLE 1

| | Concentration of $Bi(NO_3)_3 5H_2O$ used in formation of thermoelectric layer | Voltage used in formation of thermoelectric layer | Time of spinning of base fiber |
|---|---|---|---|
| Example 1 | 70 mM | 75 mV | 10 minutes |
| Example 2 | 40 mM | 75 mV | 10 minutes |
| Example 3 | 10 mM | 75 mV | 10 minutes |
| Example 4 | 5 mM | 75 mV | 10 minutes |
| Example 5 | 70 mM | 30 mV | 10 minutes |
| Example 6 | 70 mM | −6 mV | 10 minutes |
| Example 7 | 70 mM | −30 mV | 10 minutes |
| Example 8 | 70 mM | 75 mV | 5 minutes |

TABLE 1-continued

| | Concentration of $Bi(NO_3)_3 5H_2O$ used in formation of thermoelectric layer | Voltage used in formation of thermoelectric layer | Time of spinning of base fiber |
|---|---|---|---|
| Example 9 | 70 mM | 75 mV | 1 minute |
| Comparative Example 1 | 0 mM | 75 mV | 10 minutes |

The structures of the thermochemical sensors according to Comparative Examples 2 and 3 are summarized in Table 2 below.

TABLE 2

| | Substrate | Thermoelectric layer | Base fiber | Catalyst |
|---|---|---|---|---|
| Comparative Example 2 | Si | Au | Including PVP nanofibers | Pt |
| Comparative Example 3 | Si | $Bi_2Te_3$ | Not including | Pt |

FIGS. 7A-7B show optical images of the substrate according to the Example of the present invention.

Referring to FIGS. 7A and 7B, the side and top portions of the Si substrate according to Example 1 of the present invention were imaged by SEM (scanning electron microscopy). As can be seen in FIGS. 7A and 7B, it could be confirmed that the Si substrate according to Example 1 of the present invention included a plurality of the concave portions and the convex portions.

FIGS. 8A-8B show optical images of the substrate and seed layer according to the Example of the present invention.

Referring to FIG. 8A, the side and top portions of the Si substrate according to Example 1 of the present invention and the Au/Ti seed layer formed on the Si substrate were imaged by SEM. As can be seen in FIGS. 8A and 8B, it could be confirmed that the Au/Ti seed layer according to Example 1 of the present invention had an Au thickness of 80 nm and a Ti thickness of 20 nm and was conformally formed along the concave portions and the convex portions.

FIGS. 9A-9C show SEM images of the base fiber and catalyst layer according to the Example of the present invention.

Referring to FIG. 9A, the base fiber according to Example 1 of the present invention was imaged by SEM. As can be seen in FIG. 9A, it could be confirmed that the base fiber was hung over the concave portions and the convex portions, and thus at least a portion of the base fiber was spaced apart from the substrate structure by the concave portions and the convex portions.

Referring to FIG. 9B, the catalyst layer according to Example 1 of the present invention was imaged by SEM. Referring to FIG. 9C, the catalyst layer according to Example 1 was imaged at high magnification by SEM. As can be seen in FIGS. 9B and 9C, it could be seen that the catalyst layer conformally covered the thermoelectric surface of the substrate structure and the base fiber.

FIGS. 10A-10B show SEM images of the thermochemical sensor according to the Example of the present invention.

Referring to FIG. 10A, the side portion of the thermochemical sensor according to Example 1 of the present invention was imaged by SEM. Referring to FIG. 10B, the thermochemical sensor according to Example 1 of the present invention was imaged at high magnification by SEM. As can be seen in FIGS. 10A and 10B, it could be confirmed that the catalyst layer was formed to cover at least a portion of the base fiber spaced apart from the substrate structure and to surround the base fiber.

FIGS. 11 to 13 depict graphs showing characteristics depending on changes of the thermoelectric layers in the thermochemical sensors according to the Examples of the present invention and the Comparative Examples.

Referring to FIG. 11, the thermochemical sensors according to Examples 1 to 4 of the present invention and Comparative Example 1 were measured for their current density at an applied voltage ranging from −0.4 to 0.2. As can be seen in FIG. 11, it could be confirmed that the efficiency was the highest when the thermoelectric layer was formed using 70 mM $Bi(NO_3)_3 5H_2O$ according to Example 1.

Referring to FIG. 12, the thermochemical sensors according to Examples 1 to 4 of the present invention and Comparative Example 1 were measured for changes in Bi content at an applied voltage ranging from −0.4 to 0.08. As can be seen in FIG. 12, it could be confirmed that the thermoelectric layer according to the Example of the present invention showed a Bi content of 75.7 at % at a potential of −0.4 V, a Bi content of 56.5 at % at a potential of −0.09 V, a Bi content of 52.3 at % at a potential of 0.03 V, a Bi content of 56.5 at % at a potential of 0.09 V, and a Bi content of 39.6 at % at a potential of 0.72 V. Namely, it can be seen that the Bi content decreased as the potential increased.

Referring to FIG. 13, the X-ray diffraction patterns of the thermochemical sensors according to Examples 1 and Examples 5 to 7 of the present invention and Comparative Example 2 were analyzed. As can be seen in FIG. 13, it could be confirmed that the efficiency was the highest when the thermoelectric layer was formed using an applied voltage of 75 mV according to Example 1 of the present invention.

FIGS. 14A-14D show SEM images of the thermoelectric layers according to the Examples of the present invention.

Referring to FIGS. 14A to 14D, the thermoelectric layers according to Examples 1 and Examples 5 to 7 of the present invention were imaged by SEM. As can be seen in FIGS. 14A to 14D, it could be confirmed again that the efficiency was the highest when the thermoelectric layer was formed using an applied voltage of 75 mV according to Example 1 of the present invention.

FIG. 15 is a graph showing characteristics depending on the time of spinning of the base fiber in the thermochemical sensors according to the Examples of the present invention and the Comparative Example.

Referring to FIG. 15, the X-ray diffraction patterns of the thermochemical sensors according to Examples 1, 8 and 9 of the present invention and Comparative Example 3 were analyzed. As can be seen in FIG. 15, it could be confirmed that the value of I(111)/I(200) increased as the time of electrospinning of the base fiber became longer. Accordingly, it can be seen that the reaction of hydrogen with the Pt catalyst is more activated as the time of electrospinning of the base fiber becomes longer. Namely, it can be seen that as the amount of the base fiber in the thermochemical sensor according to the Example of the present invention increases, the reaction with hydrogen is more activated.

FIGS. 16A-16D and 17A-B depict graphs showing hydrogen concentration-dependent changes in the characteristics of thermochemical sensors according to the Examples of the present invention and the Comparative Examples.

Referring to FIGS. 16A to 16D, hydrogen introduction time-dependent changes in the temperatures of the thermochemical sensors according to Examples 1, 8 and 9 of the present invention and Comparative Example 3 were measured. In addition, for the case in which the catalyst was coated by performing the sputtering process for each of 20 minutes and 30 minutes, hydrogen introduction time-dependent changes in the temperatures were measured.

As can be seen in FIGS. 16A to 16D, it could be confirmed that the thermochemical sensor according to Example 1 of the present invention showed the highest temperature increase. Accordingly, it can be seen that fabricating the thermochemical sensor according to the Example of the present invention by preparing the base fiber through electrospinning for 10 minutes and coating the catalyst through the sputtering process for 30 minutes is the most efficient fabrication method.

Referring to FIG. 17A, a hydrogen introduction time-dependent change in the electromotive force of the thermochemical sensor according to Comparative Example 3 of the present invention was measured. As can be seen in FIG. 17A, it could be confirmed that the thermochemical sensor according to Comparative Example 3 showed an electromotive force of up to 0.722 µV.

Referring to FIG. 17B, a hydrogen introduction time-dependent change in the electromotive force of the thermochemical sensor according to Example 1 of the present invention was measured. As can be seen in FIG. 17B, it could be confirmed that the thermochemical sensor according to Example 1 showed an electromotive force of up to 12.7 µV. Accordingly, it can be seen that it is efficient for the thermochemical sensor according to the Example of the present invention to form the base fiber and coat the catalyst.

Although the present invention has been described in detail above with respect to the preferred embodiments thereof, the scope of the present invention is not limited to the specific embodiments described herein and shall be defined by the appended claims. In addition, those skilled in the art will appreciate that many modifications and changes are possible without departing from the scope of the present invention.

INDUSTRIAL APPLICABILITY

The thermochemical sensor according to the embodiment of the present invention can detect the presence or absence of a target gas (e.g., hydrogen gas) and sense a target gas (e.g., hydrogen gas) or the like.

The invention claimed is:

1. A thermochemical sensor comprising:
a substrate structure comprising a surface comprising concave portions and convex portions, said surface being a thermoelectric surface;
a base fiber disposed on the thermoelectric surface of the substrate structure; and
a catalyst layer which conformally covers the thermoelectric surface of the substrate structure and the base fiber.

2. The thermochemical sensor of claim 1, wherein the base fiber is hung over the concave portions and the convex portions, so that at least a portion of the base fiber is spaced apart from the substrate structure by the concave portions and the convex portions.

3. The thermochemical sensor of claim 2, wherein the catalyst layer is configured to cover the at least a portion of the base fiber spaced apart from the substrate structure.

4. The thermochemical sensor of claim 1, wherein the catalyst layer is configured to surround the base fiber.

5. The thermochemical sensor of claim 1, wherein the catalyst layer is configured to react with a target gas, and a proportion of a crystal surface of the catalyst layer that reacts with the target gas is proportional to an amount of the base fiber.

6. The thermochemical sensor of claim 5, wherein the crystal surface of the catalyst layer comprises a (111) plane of the catalyst layer.

7. The thermochemical sensor of claim 5, wherein, when the catalyst layer reacts with the target gas, heat is generated in the catalyst layer, and due to the generated heat, an electrical signal is generated in the thermoelectric layer.

8. The thermochemical sensor of claim 1, wherein the substrate structure comprises:
   a substrate having concave portions and convex portions; and
   a thermoelectric layer which conformally covers the substrate and which provides the thermoelectric surface.

9. The thermochemical sensor of claim 8, wherein a thickness of the thermoelectric layer is thinner than a level difference between the concave portions of the thermoelectric surface and the convex portions of the thermoelectric surface.

10. The thermochemical sensor of claim 8, wherein the thermoelectric layer comprises a chalcogenide-based material.

11. The thermochemical sensor of claim 8, wherein the thermoelectric layer comprises $Bi_2Te_3$.

12. The thermochemical sensor of claim 1, wherein the base fiber comprises a polymer, wherein the polymer comprises any one of PVP (polyvinylpyrrolidone), polyethylene oxide, polyvinyl acetate, polyvinyl alcohol, polylactic acid, polyamide, polyester, and polypropylene.

13. A method for fabricating a thermochemical sensor, comprising the steps of:
    forming a substrate structure comprising a surface having concave portions and convex portions, said surface being a thermoelectric surface;
    forming a base fiber disposed on the thermoelectric surface of the substrate structure; and
    forming a catalyst layer which conformally covers the thermoelectric surface of the substrate structure and the base fiber.

14. The method of claim 13, wherein the step of forming the substrate structure comprises the steps of:
    preparing a substrate having concave portions and convex portions; and
    forming on the substrate a thermoelectric layer which provides the thermoelectric surface.

15. The method of claim 14, wherein the step of preparing the substrate having concave portions and convex portions comprises the steps of:
    preparing a preliminary substrate;
    immersing the preliminary substrate in an aqueous etching solution; and
    heat-treating the immersed preliminary substrate.

16. The method of claim 13, wherein the step of forming the base fiber comprises a step of spinning a polymer solution onto the thermoelectric surface of the substrate structure.

* * * * *